United States Patent
Stark et al.

(10) Patent No.: US 9,468,212 B2
(45) Date of Patent: Oct. 18, 2016

(54) ANTIFUNGAL COMPOSITIONS

(71) Applicant: DSM IP ASSETS B.V., Heerlen (NL)

(72) Inventors: Jacobus Stark, Echt (NL); Eva Louise Wilhelmine Sack, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/760,276

(22) PCT Filed: Jan. 13, 2014

(86) PCT No.: PCT/EP2014/050443
§ 371 (c)(1),
(2) Date: Jul. 10, 2015

(87) PCT Pub. No.: WO2014/108527
PCT Pub. Date: Jul. 17, 2014

(65) Prior Publication Data
US 2015/0351404 A1  Dec. 10, 2015

(30) Foreign Application Priority Data

Jan. 14, 2013 (EP) .................... 13151116
Apr. 24, 2013 (EP) .................... 13165085

(51) Int. Cl.
*A01N 43/90* (2006.01)
*A01N 43/36* (2006.01)

(52) U.S. Cl.
CPC .............. *A01N 43/90* (2013.01); *A01N 43/36* (2013.01)

(58) Field of Classification Search
CPC combination set(s) only.
See application file for complete search history.

(56) References Cited

U.S. PATENT DOCUMENTS

2008/0039319 A1* 2/2008 Blettner ............... A01N 43/90
504/100

FOREIGN PATENT DOCUMENTS

| WO | WO 2004/105491 | * | 12/2004 |
| WO | 2005041666 A1 | | 5/2005 |
| WO | WO 2009/077613 | * | 6/2009 |
| WO | 2012117055 A1 | | 9/2012 |

OTHER PUBLICATIONS

International Search Report from corresponding PCT/EP2014/050443, mailed Mar. 20, 2014.
"4129. Fludioxonil" In: "The Merck Index, 14th edition", Jan. 1, 2006, Whitehouse Station, NJ, XP055063870, p. 706.
"3989. Fenpiclonil "In: "The Merck Index, 14th edition", Jan. 1, 2006, Merck & Co., Whitehouse Station, NJ , U.S .A., XP055063873, ISBN: 978-0-91-191000-1, pp. 681-682, Entry No. 3989; p. 681.
"6427. Natamycin" In: "The Merck Index, 14th edition", Jan. 1, 2006, Merck & Co., Whitehouse Station, NJ , U.S.A., XP055063866, ISBN: 978-0-91-191000-1 page 1111, Entry No. 6427; p. 1111.
Hondrodimou et al.: "Efficacy of natamycin to control fungal growth in natural black olive fermentation", Food Microbiology, Academic Press Ltd, London, GB, Vol . 28, No. 3, Nov. 23, 2010, pp. 621-627, XP028174460.
Chong et al.: "Macrolideantibiotic studies. XVI I. Cyclichemiketal structures in nystatin, amphotericin B, pimaricin and lucensomycin", Tetrahedron Letters, Elsevier, Amsterdam, NL, vol. 13, No. 49, Jan. 1, 1972, pp. 5053-5056, XP027191251.
5592. Lucensomycin In: "The Merck Index, 14th edition" Jan. 1, 2006, Merck & Co., Whitehouse Station, NJ , U. S .A., XP055063894.
Iacomi-Vasilescu et al., "In vitro fungicide sensitivity of Alternaria species pathogenic to crucifers and identification of *Alternaria brassicicola* field isolates highly resistant to both dicarboximides and phenylpyrroles", Elsevier, ScienceDirect, Crop Protection 23, 2004, pp. 481-488.
Kanetis et al., "Fludioxonil-resistant isolates of Penicillium digitatum show diverse fitness and no relationship to osmotic stress regulation", Department of Plant Pathology, University of California, 2006, 1 page.
Kinay, et al., "Characterization of fungicide-resistant isolates of Penicillium digitatum collected in California", Elsevier, ScienceDirect, Crop Protection 26, 2007, pp. 647-656.

* cited by examiner

*Primary Examiner* — John Pak
(74) *Attorney, Agent, or Firm* — McBee Moore Woodward & Vanik IP, LLC

(57) ABSTRACT

The present invention relates to new antifungal compositions and their use in the treatment of agricultural products.

18 Claims, No Drawings

ANTIFUNGAL COMPOSITIONS

CROSS REFERENCE TO RELATED APPLICATIONS

This application is a §371 National Stage Application of PCT/EP2014/050443, filed 13 Jan. 2014, which claims priority to EP 13151116.4, filed 14 Jan. 2013 and EP 13165085.5, filed 24 Apr. 2013.

BACKGROUND

1. Field of the Invention

The present invention discloses new antimicrobial compositions to control plant diseases and to prevent microbial spoilage of crops.

2. Description of Related Art

It is estimated that about 25% of the world crop production is lost due to microbial spoilage, of which spoilage by fungi is by far the most important cause. Not only from an economical point of view, but also from a humane point of view it is of great importance to prevent spoilage of food products. After all, in many parts of the world people suffer from hunger.

Success in combating plant and crop diseases and in reducing the damage they cause to yields and quality depends greatly on the timely application of fungicides. The prolonged and frequent use of many fungicides such as e.g. benzamidazoles has contributed to reduce their effectiveness thanks to the development of phenomena of resistance.

Over the past forty years new classes of fungicides have been developed and marketed. One of those classes is the class of phenylpyrroles.

Phenylpyrrole fungicides have not been immune to challenges in their development and maintenance. A large concern has been resistance development. Resistance to phenylpyrrole fungicides has been observed on several diseases now (see Iacomi-Vasilescu et al., 2004; Kanetis et al., 2006; Kinay et al., 2007).

For many decades, the polyene macrolide antimycotic natamycin has been used to prevent fungal growth on food products such as cheeses and sausages. This natural preservative, which is produced by fermentation using *Streptomyces natalensis*, is widely used throughout the world as a food preservative and has a long history of safe use in the food industry. It is very effective against all known food spoilage fungi. Although natamycin has been applied for many years in e.g. the cheese industry, up to now development of resistant fungal species has never been observed.

Consequently, it can be concluded that there is a severe need for more effective antimicrobial compositions, e.g. antifungal compositions, for the treatment of fungal growth in and on plants and crops.

SUMMARY

The present invention solves the problem by providing a new synergistic antimicrobial, e.g. antifungal, composition comprising a polyene antifungal compound and at least one antifungal compound from the family of phenylpyrrole fungicides. As used herein, the term "synergistic" means that the combined effect of the antifungal compounds when used in combination is greater than their additive effects when used individually.

In general, synergistic activity of two active ingredients can be tested in for example the analysis of variance model using the treatment interaction stratum (see Slinker, 1998).

Relative efficacy can be calculated by means of the following formula: ((value of evolution status of untreated control−value of evolution status of composition)/(value of evolution status of untreated control))*100. An interaction coefficient can then be calculated by means of the following formula: ((relative efficacy of combination compound A+compound B)/(relative efficacy of compound A+relative efficacy of compound B))*100. An interaction coefficient larger than 100 indicates synergy between the compounds.

Alternatively, synergy can be calculated as follows: the antifungal activity (in %) of the individual active ingredients can be determined by calculating the reduction in mould growth observed on products treated with the active ingredients in comparison to the mould growth on products treated with a control composition. The expected antifungal activity (E in %) of the combined antifungal composition comprising both active ingredients can be calculated according to the Colby equation (Colby, 1967): $E=X+Y-[(X \cdot Y)/100]$, wherein X and Y are the observed antifungal activities (in %) of the individual active ingredients X and Y, respectively. If the observed antifungal activity (O in %) of the combination exceeds the expected antifungal activity (E in %) of the combination and the synergy factor O/E is thus >1.0, the combined application of the active ingredients leads to a synergistic antifungal effect.

DETAILED DESCRIPTION OF A PREFERRED EMBODIMENT

In an embodiment of the invention, the at least one antifungal compound from the family of phenylpyrrole fungicides is selected from the group consisting of fludioxonil and fenpiclonil.

In an embodiment the compositions may also contain two or more different antifungal compounds from the family of phenylpyrrole fungicides. It is to be understood that derivatives of antifungal compounds from the family of phenylpyrrole fungicides including, but not limited to, salts or solvates of antifungal compounds from the family of phenylpyrrole fungicides or modified forms of antifungal compounds from the family of phenylpyrrole fungicides may also be applied in the compositions of the invention. Examples of commercial products containing phenylpyrrole fungicides such as fludioxonil are products with the brand names Maxim®, Celest® and Switch®. Examples of commercial products containing phenylpyrrole fungicides such as fenpiclonil are products with the brand names Beret®, Galbas® and Gambit®. Said commercial products can be incorporated in the present invention.

In an embodiment the polyene antifungal compound is selected from the group consisting of natamycin, nystatin, amphotericin B, trienin, etruscomycin, filipin, chainin, dermostatin, lymphosarcin, candicidin, aureofungin A, aureofungin B, hamycin A, hamycin B and lucensomycin. In a preferred embodiment the polyene antifungal compound is natamycin. In an embodiment the compositions may also contain two or more different polyene antifungal compounds. It is to be understood that derivatives of polyene antifungal compounds including, but not limited to, salts or solvates of polyene antifungal compounds or modified forms of polyene antifungal compounds may also be applied in the compositions of the invention. Examples of commercial products containing natamycin are the products with the brand name Delvocid®. Such products are produced by DSM Food Specialties (The Netherlands) and may be solids containing e.g. 50% (w/w) natamycin or liquids comprising between e.g. 2-50% (w/v) natamycin. Said commercial products can be incorporated in the compositions of the invention.

The composition of the present invention generally comprises from about 0.005 g/l to about 100 g/l and preferably from about 0.01 g/l to about 50 g/l of a polyene antifungal compound. Preferably, the amount is from 0.01 g/l to 3 g/l.

The composition of the present invention generally comprises from about 0.0001 g/l to about 2000 g/l and preferably from about 0.0005 g/l to about 1500 g/l of an antifungal compound from the family of phenylpyrrole fungicides. More preferably, the amount is from 0.001 g/l to 1000 g/l.

In an embodiment the composition of the present invention further comprises at least one additional compound selected from the group consisting of a sticking agent, a carrier, a colouring agent, a protective colloid, an adhesive, a herbicide, a fertilizer, a thickening agent, a sequestering agent, a thixotropic agent, a surfactant, a further antimicrobial compound, a detergent, a preservative, a spreading agent, a filler, a spray oil, a flow additive, a mineral substance, a solvent, a dispersant, an emulsifier, a wetting agent, a stabiliser, an antifoaming agent, a buffering agent, an UV-absorber and an antioxidant. A further antimicrobial antifungal compound may be an antifungal compound (e.g. imazalil, thiabendazole) or a compound to combat insects, nematodes, mites and/or bacteria. Of course, the compositions according to the invention may also comprise two or more of any of the above additional compounds. Any of the above mentioned additional compounds may also be combined with the polyene antifungal compound and/or the at least one antifungal compound from the family of phenylpyrrole fungicides in case the antifungal compounds are applied separately. In an embodiment the additional compounds are additives acceptable for the specific use, e.g. food, feed, medicine, cosmetics or agriculture. Additional compounds suitable for use in food, feed, medicine, cosmetics or agriculture are known to the person skilled in the art.

In a specific embodiment the further antimicrobial compound is a natural crop protection compound belonging to the group of phosphites, e.g. $KH_2PO_3$ or $K_2HPO_3$ or a mixture of both phosphite salts. Phosphite containing compounds as used herein means compounds comprising a phosphite group, i.e. $PO_3$ (in the form of e.g. $H_2PO_3^-$, $HPO_3^{2-}$ or $PO_3^{3-}$) or any compound which allows the release of a phosphite ion including compounds such as phosphorous acid and phosphonic acid as well as derivatives thereof such as esters and/or alkali metal or alkaline earth metal salts thereof. In case the compositions of the present invention comprise a polyene antifungal compound (e.g. natamycin) and at least one phosphite containing compound, they preferably comprise 0.1 g or less lignosulphonate, more preferably 0.1 g or less polyphenol, per gram polyene antifungal compound. Preferably, they comprise 0.01 g or less lignosulphonate, more preferably 0.01 g or less polyphenol, per gram polyene antifungal compound. In particular, they are free of lignosulphonate and preferably free of polyphenol. Suitable examples of phosphite containing compounds are phosphorous acid and its (alkali metal or alkaline earth metal) salts such as potassium phosphites e.g. $KH_2PO_3$ and $K_2HPO_3$, sodium phosphites and ammonium phosphites, and ($C_1$-$C_4$) alkyl esters of phosphorous acid and their salts such as aluminum ethyl phosphite (fosetyl-Al), calcium ethyl phosphite, magnesium isopropyl phosphite, magnesium isobutyl phosphite, magnesium sec-butyl phosphite and aluminum N-butyl phosphite. Of course, mixtures of phosphite containing compounds are also encompassed. A mixture of e.g. $KH_2PO_3$ and $K_2HPO_3$ can easily be obtained by e.g. adding KOH or $K_2CO_3$ to a final pH of 5.0-6.0 to a $KH_2PO_3$ solution. As indicated above, precursor-type compounds which in the crop or plant are metabolized into phosphite compounds can also be included in the compositions of the present invention. Examples are phosphonates such as the fosetyl-aluminium complex. In e.g. a crop or plant the ethyl phosphonate part of this molecule is metabolized into a phosphite. An example of such a compound in the commercial ethyl hydrogen phosphonate product called Aliette® (Bayer, Germany). The ratio of phosphite to natamycin (in weight) in the compositions is in general between 2:1 to 500:1 (w/w), preferably between 3:1 to 300:1 (w/w) and more preferably between 5:1 to 200:1 (w/w).

Compositions according to the invention may have a pH of from 1 to 10, preferably of from 2 to 9, more preferably of from 3 to 8 and most preferably of from 4 to 7. They may be solid, e.g. powder compositions, or may be liquid. The compositions of the present invention can be aqueous or non-aqueous ready-to-use compositions, but may also be aqueous or non-aqueous concentrated compositions/suspensions or stock compositions, suspensions and/or solutions which before use have to be diluted with a suitable diluent such as water or a buffer system. Alternatively, the compositions of the invention can also be used to prepare coating emulsions. The compositions of the present invention can also have the form of concentrated dry products such as e.g. powders, granulates and tablets. They can be used to prepare compositions for immersion or spraying of products such as agricultural products including plants, crops, vegetables and/or fruits. Of course, the above is also applicable when the polyene antifungal compound and the at least one antifungal compound from the family of phenylpyrrole fungicides are applied as separate compositions.

In a further aspect the invention relates to a kit comprising a polyene antifungal compound and at least one antifungal compound from the family of phenylpyrrole fungicides. The polyene antifungal compound and the at least one antifungal compound from the family of phenylpyrrole fungicides may be present in two separate packages, e.g. containers. The components of the kit may be either in dry form or liquid form in the package. If necessary, the kit may comprise instructions for dissolving the compounds. In addition, the kit may contain instructions for applying the compounds.

In a further aspect the invention pertains to a method for protecting a product against fungi by treating the product with a polyene antifungal compound and at least one antifungal compound from the family of phenylpyrrole fungicides. In addition, the product can be treated with other antifungal and/or antimicrobial compounds either prior to, concomitant with or after treatment of the products with the polyene antifungal compound and the at least one antifungal compound from the family of phenylpyrrole fungicides. The product may be treated by sequential application of the polyene antifungal compound and the at least one antifungal compound from the family of phenylpyrrole fungicides or vice versa. Alternatively, the product may be treated by simultaneous application of the polyene antifungal compound and the at least one antifungal compound from the family of phenylpyrrole fungicides. In case of simultaneous application, the compounds can be present in different compositions that are applied simultaneously or the compounds may be present in a single composition. In yet another embodiment the product may be treated by separate or alternate modes of applying the antifungal compounds. In an embodiment the invention is directed to a process for the treatment of products by applying the polyene antifungal compound and the at least one antifungal compound from the family of phenylpyrrole fungicides to the products. By applying the compounds fungal growth on or in the products can be prevented. In other words, the compounds protect the products from fungal growth and/or from fungal infection and/or from fungal spoilage. The compounds can also be used to treat products that have been infected with a fungus. By applying the compounds the disease development due to fungi on or in these products can be slowed down, stopped or the products may even be cured from the disease. In an embodiment of the invention the products are treated with a composition or kit according to the invention. In an embodiment the product is a food, feed, pharmaceutical, cosmetic or agricultural product. In a preferred embodiment the product is an agricultural product.

The polyene antifungal compound and the at least one antifungal compound from the family of phenylpyrrole fungicides, the compositions according to the invention and the kits according to the invention can be applied to the products by spraying. Other methods suitable for applying these compounds, compositions and kits in liquid form to the products are also a part of the present invention. These include, but are not limited to, dipping, watering, drenching, introduction into a dump tank, vaporizing, atomizing, fogging, fumigating, painting, brushing, dusting, foaming, spreading-on, packaging and coating (e.g. by means of wax or electrostatically). In addition, the antifungal compounds may also be injected into the soil. Spraying applications using automatic systems are known to reduce the labour costs and are cost-effective. Methods and equipment well-known to a person skilled in the art can be used for that purpose. The compositions according to the invention can be regularly sprayed, when the risk of infection is high. When the risk of infection is lower spray intervals may be longer. Depending on the type of application, the amount of polyene antifungal compound applied may vary from 5 ppm to 10,000 ppm, preferably from 10 ppm to 5,000 ppm and most preferably from 20 to 1,000 ppm. Depending on the type of application, the amount of the at least one antifungal compound from the family of phenylpyrrole fungicides applied may vary from 10 ppm to 5,000 ppm, preferably from 20 ppm to 3,000 ppm and most preferably from 50 to 1,000 ppm.

In a specific embodiment the agricultural product can be treated post-harvest. By using a polyene antifungal compound and the at least one antifungal compound from the family of phenylpyrrole fungicides the control of post-harvest and/or storage diseases is achieved for a long period of time to allow transport of the harvested agricultural product over long distances and under various storage conditions with different controlled atmosphere systems in respect of temperature and humidity. Post-harvest storage disorders are e.g. lenticel spots, scorch, senescent breakdown, bitter pit, scald, water core, browning, vascular breakdown, $CO_2$ injury, $CO_2$ or $O_2$ deficiency, and softening. Fungal diseases may be caused for example by the following fungi: *Blumeria* spp., e.g. *Blumeria graminis*; *Uncinula* spp., e.g. *Uncinula necator*; *Leveillula* spp., e.g. *Leveillula taurica*; *Podosphaera* spp., e.g. *Podosphaera leucotricha, Podosphaera fusca, Podosphaera aphanis*; *Microsphaera* spp., e.g. *Microsphaera syringae*; *Sawadaea* spp., e.g. *Sawadaea tulasnei*; *Mycosphaerella* spp., *Mycosphaerella musae, Mycosphaerella fragariae, Mycosphaerella citri*; *Mucor* spp., e.g. *Mucor piriformis*; *Monilinia* spp., e.g. *Monilinia fructigena, Monilinia laxa*; *Phomopsis* spp., *Phomopsis natalensis*; *Colletotrichum* spp., e.g. *Colletotrichum musae, Colletotrichum gloeosporioides, Colletotrichum coccodes*; *Verticillium* spp., e.g. *Verticillium theobromae*; *Nigrospora* spp.; *Botrytis* spp., e.g. *Botrytis cinerea*; *Diplodia* spp., e.g. *Diplodia citri*; *Pezicula* spp.; *Alternaria* spp., e.g. *Alternaria citri, Alternaria alternata*; *Septoria* spp., e.g. *Septoria depressa*; *Venturia* spp., e.g. *Venturia inaequalis, Venturia pyrina*; *Rhizopus* spp., e.g. *Rhizopus stolonifer, Rhizopus oryzae*; *Glomerella* spp., e.g. *Glomerella cingulata*; *Sclerotinia* spp., e.g. *Sclerotinia fruiticola*; *Ceratocystis* spp., e.g. *Ceratocystis paradoxa*; *Fusarium* spp., e.g. *Fusarium semitectum, Fusarium moniliforme, Fusarium solani, Fusarium oxysporum*; *Cladosporium* spp., e.g. *Cladosporium fulvum, Cladosporium cladosporioides, Cladosporium cucumerinum, Cladosporium musae*; *Penicillium* spp., e.g. *Penicillium funiculosum, Penicillium expansum, Penicillium digitatum, Penicillium italicum*; *Phytophthora* spp., e.g. *Phytophthora citrophthora, Phytophthora fragariae, Phytophthora cactorum, Phytophthora parasitica*; *Phacydiopycnis* spp., e.g. *Phacydiopycnis malirum*; *Gloeosporium* spp., e.g. *Gloeosporium album, Gloeosporium perennans, Gloeosporium fructigenum, Gloeosporium singulata*; *Geotrichum* spp., e.g. *Geotrichum candidum*; *Phlyctaena* spp., e.g. *Phlyctaena vagabunda*; *Cylindrocarpon* spp., e.g. *Cylindrocarpon mali*; *Stemphyllium* spp., e.g. *Stemphyllium vesicarium*; *Thielaviopsis* spp., e.g. *Thielaviopsis paradoxy*; *Aspergillus* spp., e.g. *Aspergillus niger, Aspergillus carbonarius*; *Nectria* spp., e.g. *Nectria galligena*; *Cercospora* spp., e.g. *Cercospora angreci, Cercospora apii, Cercospora atrofiliformis, Cercospora musae, Cercospora zeae-maydis*.

Another aspect of the present invention relates to the use of a polyene antifungal compound and at least one antifungal compound from the family of phenylpyrrole fungicides to protect a product against fungi. As indicated above, the compounds may be used, e.g. applied, sequentially or simultaneously. In an embodiment the invention relates to a use, wherein a composition or kit according to the invention is applied to the product. In an embodiment the product is a food, feed, pharmaceutical, cosmetic or agricultural product. In a preferred embodiment the product is an agricultural product.

In a specific embodiment the polyene antifungal compound and at least one antifungal compound from the family of phenylpyrrole fungicides can be used in medicine, e.g. to treat and/or prevent fungal diseases. The polyene antifungal compound and at least one antifungal compound from the family of phenylpyrrole fungicides can for instance be used in the form of a pharmaceutical composition. The composition may further comprise pharmaceutically acceptable excipients. The antifungal compounds may be administered orally or parenterally. The type of composition is dependent on the route of administration.

A further aspect of the invention is directed to a product treated with a polyene antifungal compound and at least one antifungal compound from the family of phenylpyrrole fungicides. In an embodiment the product is treated with a composition or kit according to the invention. The invention is therefore directed to a product comprising a polyene antifungal compound and at least one antifungal compound from the family of phenylpyrrole fungicides. The treated products may comprise a polyene antifungal compound and at least one antifungal compound from the family of phenylpyrrole fungicides on their surface and/or inside the product. Alternatively, the treated products may comprise a coating comprising these compounds. In an embodiment the treated products comprise from 0.000001 to 200 mg/dm$^2$, preferably 0.00001 to 100 mg/dm$^2$, more preferably from 0.00005 to 10 mg/dm$^2$ of the polyene antifungal compound on their surface. In a further embodiment they comprise from 0.000001 to 200 mg/dm$^2$, preferably 0.00001 to 100 mg/dm$^2$, more preferably from 0.00005 to 10 mg/dm$^2$ of the at least one antifungal compound from the family of phenylpyrrole fungicides on their surface. In an embodiment the product is a food, feed, pharmaceutical, cosmetic or agricultural product. In a preferred embodiment the product is an agricultural product.

The term "food products" as used herein is to be understood in a very broad sense and includes, but is not limited to, cheese, cream cheese, shredded cheese, cottage cheese processed cheese, sour cream, dried fermented meat product including salamis and other sausages, wine, beer, yoghurt, juice and other beverages, salad dressing, cottage cheese dressing, dips, bakery products and bakery fillings, surface glazes and icing, spreads, pizza toppings, confectionery and confectionery fillings, olives, olive brine, olive oil, juices, tomato purees and paste, condiments, and fruit pulp and the like food products.

The term "feed products" as used herein is also to be understood in a very broad sense and includes, but is not limited to, pet food, broiler feed, etc.

The term "pharmaceutical product" as used herein is also to be understood in a very broad sense and includes products comprising an active molecule such as a drug, agent, or pharmaceutical compound and optionally a pharmaceutically acceptable excipient, i.e. any inert substance that is combined with the active molecule for preparing an agreeable or convenient dosage form.

The term "cosmetic product" as used herein is also to be understood in a very broad sense and includes products that are used for protecting or treating horny tissues such as skin and lips, hair and nails from drying by preventing transpiration of moisture thereof and further conditioning the tissues as well as giving good appearance to these tissues. Products contemplated by the term "cosmetic product" include, but are not limited to, moisturizers, personal cleansing products, occlusive drug delivery patches, nail polish, powders, wipes, hair conditioners, skin treatment emulsions, shaving creams and the like.

The term "agricultural products" as used herein is also to be understood in a very broad sense and includes, but is not limited to, cereals, e.g. wheat, barley, rye, oats, rice, sorghum and the like; beets, e.g. sugar beet and fodder beet; pome and stone fruit and berries, e.g. apples, pears, plums, apricots, peaches, almonds, cherries, strawberries, raspberries and blackberries; leguminous plants, e.g. beans, lentils, peas, soy beans; oleaginous plants, e.g. rape, mustard, poppy, olive, sunflower, coconut, castor-oil plant, cocoa, ground-nuts; cucurbitaceae, e.g. pumpkins, gherkins, melons, cucumbers, squashes, aubergines; fibrous plants, e.g. cotton, flax, hemp, jute; citrus fruit, e.g. oranges, lemons, grapefruits, mandarins, limes; tropical fruit, e.g. papayas, passion fruit, mangos, carambolas, pineapples, bananas, kiwis; vegetables, e.g. spinach, lettuce, asparagus, brassicaceae such as cabbages and turnips, carrots, onions, tomatoes, potatoes, seed-potatoes, hot and sweet peppers; laurel-like plants, e.g. avocado, cinnamon, camphor tree; or products such as maize, tobacco, nuts, coffee, sugarcane, tea, grapevines, hops, rubber plants, as well as ornamental plants, e.g. cut flowers, roses, tulips, lilies, narcissus, crocuses, hyacinths, dahlias, gerbera, carnations, fuchsias, chrysanthemums, and flower bulbs, shrubs, deciduous trees and evergreen trees such as conifers, plants and trees in greenhouses. It includes, but is not limited to, plants and their parts, fruits, seeds, cuttings, cultivars, grafts, bulbs, tubers, root-tubers, rootstocks, cut flowers and vegetables.

A method for preparing a composition as described herein is another aspect of the present invention. The method comprises adding a polyene antifungal compound to at least one antifungal compound from the family of phenylpyrrole fungicides. The compounds may for instance be added separately to an aqueous composition and mixed, followed, if necessary, by adjustment of the pH, viscosity, etc. If added separately, some or all of the separate compounds may be in powder form, but alternatively some or all may also be in liquid form. The compounds may for instance also be added to one another in powder form and mixed to obtain a powdered composition. The powdered composition may then be added to an aqueous composition.

EXAMPLES

Example 1

Treatment of Bananas

Four organic, unripe (green) bananas are used per treatment. The peel of each banana is wounded thrice using a cork borer according to the method described by de Lapeyre de Bellaire and Dubois (1987). Subsequently, each wound is inoculated with 15 µl of a *Fusarium proliferatum* suspension containing 1×10$^5$ of spores/ml. After incubation for 4 hours at 20° C., each banana wound is treated with 100 µl of a freshly prepared aqueous antifungal composition comprising either natamycin (DSM Food Specialties, Delft, The Netherlands), fludioxonil or both. In addition, the phenylpyrrole fungicide fenpiclonil alone or in combination with natamycin is tested. The antifungal compositions comprise 1.00% (w/w) methylhydroxyethylcellulose (MHEC), 0.40% (w/w) xanthan gum, 0.20% (w/w) anti-foaming agent, 0.30% (w/w) citric acid, 0.39% (w/w) lactic acid and 0.11% (w/w) potassium sorbate. The pH of the composition is 4.0. A composition without natamycin or a phenylpyrrole fungicide is used as control. The treated, unripe bananas are incubated in a closed box in the dark at 20° C. and a relative air humidity of 95%, which is obtained in the presence of a saturated Na$_2$HPO$_4$ aqueous solution. During the first 20 days of incubation, a ripe (yellow) banana is included in the closed box to elevate the ethylene gas level and thus induce ripening of the treated, unripe bananas.

During incubation, the degree of mould growth on the bananas is assessed in a twofold manner: (i) the number of moulded wounds per total of 12 wounds is counted; and (ii) the antifungal activity (in %) of the individual active ingredients is determined by calculating the reduction in mould growth observed on the banana wounds treated with the antifungal composition in comparison to the mould growth on the banana wounds treated with the control composition. The expected antifungal activity (E in %) of the combined antifungal composition comprising both active ingredients is calculated according to the Colby equation (Colby, 1967):

$$E = X + Y - [(X \cdot Y)/100]$$

wherein X and Y are the observed antifungal activities (in %) of the individual active ingredients X and Y, respectively. If the observed antifungal activity (O in %) of the combination exceeds the expected antifungal activity (E in %) of the combination and the synergy factor O/E is thus >1.0, the combined application of the active ingredients leads to a synergistic antifungal effect.

The results clearly demonstrate that the antifungal composition comprising both natamycin and a phenylpyrrole fungicide protect bananas better against mould growth than natamycin or a phenylpyrrole fungicide alone.

Hence, the combination of natamycin and a phenylpyrrole fungicide has synergistic antifungal activity on bananas.

Example 2

Treatment of Strawberries

Twelve fresh, organic strawberries are used per treatment. Each strawberry is wounded with a 0.5 mm long cut and each wound is inoculated with 10 µl of a *Botrytis cinerea* suspension containing $1 \times 10^5$ of spores/ml. After a 2-hour incubation period at 20° C., each strawberry is dipped individually for 1 minute in a freshly prepared aqueous antifungal composition comprising either natamycin (DSM Food Specialties, Delft, The Netherlands), fludioxonil or both. In addition, the phenylpyrrole fungicide fenpiclonil alone or in combination with natamycin is tested. The antifungal compositions also comprise 1.00% (w/w) methylhydroxyethylcellulose (MHEC), 0.40% (w/w) xanthan gum, 0.20% (w/w) anti-foaming agent, 0.30% (w/w) citric acid, 0.39% (w/w) lactic acid and 0.11% (w/w) potassium sorbate. The pH of the composition is 4.0. A composition without natamycin or a phenylpyrrole fungicide is used as control. The treated strawberries are incubated in a closed box in the dark at 20° C.

After incubation, the mould growth on the strawberries is assessed in a twofold manner: (i) the number of moulded strawberries per total of 12 strawberries is counted; and (ii) the antifungal activity (in %) of the individual and combined active ingredients is determined by calculating the reduction in mould growth observed on the strawberries treated with the antifungal composition in comparison to the mould growth on the strawberries treated with the control composition according to the Colby method described in Example 1 (Colby, 1967).

The results demonstrate that the antifungal composition comprising natamycin and a phenylpyrrole fungicide have a stronger antifungal activity on strawberries than natamycin or a phenylpyrrole fungicide alone.

Hence, the combined application of natamycin and a phenylpyrrole fungicide synergistically reduces mould growth on strawberries.

Example 3

Treatment of Mandarins

Ten fresh, organic mandarins are used per treatment. The peel of each mandarin is wounded once using a cork borer according to the method described by de Lapeyre de Bellaire and Dubois (1987). Subsequently, each wound is inoculated with 10 µl of a *Penicillium italicum* suspension containing $1 \times 10^4$ of spores/ml. After incubation for 2 hours at 20° C., the mandarins are dipped individually for 1 minute in a freshly prepared aqueous antifungal composition comprising either natamycin (DSM Food Specialties, Delft, The Netherlands), fludioxonil or both. In addition, the phenylpyrrole fungicide fenpiclonil alone or in combination with natamycin is tested. In addition, the antifungal compositions comprise 3.1% (w/w) beeswax, 0.76% (w/w) glycerol, 0.66% (w/w) polyoxyethylene sorbitan monostearate (Tween 60), 0.03% (w/w) methylhydroxyethylcellulose (MHEC), 0.02% (w/w) xanthan gum, 0.02% (w/w) anti-foaming agent, 0.15% (w/w) citric acid and 0.01% (w/w) potassium sorbate. The pH of the composition is 4.0. A composition without natamycin or a phenylpyrrole fungicide is used as control.

The treated mandarins are incubated in a closed box in the dark at 20° C. and assessed on mould growth after 25, 28, 31 and 34 days of incubation. The antifungal activity (in %) of the individual and combined active ingredients is determined by calculating the reduction in mould growth observed on the mandarins treated with the antifungal composition in comparison to the mould growth on the mandarins treated with the control composition according to the Colby method (Colby, 1967) described in Example 1 and 2.

The results prove that the antifungal composition comprising natamycin and a phenylpyrrole fungicide is superior to the compositions comprising natamycin or a phenylpyrrole fungicide alone in preventing mould growth on mandarins.

Thus, the combined application of natamycin and a phenylpyrrole fungicide synergistically reduces mould growth on mandarins.

Example 4

In Vitro Antifungal Activity

To demonstrate synergistic antifungal activity of the combination of natamycin with a phenylpyrrole fungicide against *Botrytis cinerea*, an in vitro assay is conducted using 96-well microtiter plates. The following compositions are tested:
Control (no active ingredient),
natamycin (DSM Food Specialties, Delft, The Netherlands),
a phenylpyrrole fungicide,
natamycin+a phenylpyrrole fungicide.

After filling each well of a microtiter plate with 92 µl of PCB medium, the active ingredient(s) are added from separate stock solutions prepared in PCB medium or methanol, which resulted in an intermediate volume of 100 µl per well. Subsequently, 100 µl of a *Botrytis cinerea* suspension prepared in PCB medium is used to inoculate each well with $2.5 \times 10^3$ spores/ml. Each well thus contains a final volume of 200 µl and <1% of methanol, which does not affect growth of *Botrytis cinerea* (data not shown).

After incubation of the microtiter plates at 25° C., the in vitro antifungal activity (%) of the individual active ingredients is assessed by calculating the reduction in mould growth observed in the presence of the active ingredient in comparison to the mould growth observed in the absence of the active ingredient. The expected antifungal activity (E in %) of the active ingredient combination is calculated according to the Colby equation (Colby, 1967):

$$E = X + Y - [(X \cdot Y)/100]$$

wherein X and Y are the observed antifungal activities (in %) of the individual active ingredients X and Y, respectively. If the observed antifungal activity (O in %) of the combination exceeds the expected antifungal activity (E in %) of the combination and the resulting synergy factor O/E is thus >1.0, the combined application of the active ingredients leads to a synergistic antifungal effect.

The results demonstrate that both the natamycin+phenylpyrrole fungicide combination have much stronger antifungal activity against *Botrytis cinerea* than natamycin and a phenylpyrrole fungicide individually.

Hence, the combined application of natamycin and a phenylpyrrole fungicide synergistically inhibits growth of *Botrytis cinerea*.

Example 5

Treatment of Strawberries

Twelve fresh, organic strawberries were used per treatment. Each strawberry was wounded with a 0.5 mm long cut and each wound was inoculated with 10 µl of a *Botrytis cinerea* suspension containing $1 \times 10^5$ of spores/ml. After a 3-hour incubation period at 20° C., each strawberry was dipped individually for 1 minute in a freshly prepared aqueous antifungal composition comprising either 500 ppm natamycin (DSM Food Specialties, Delft, The Netherlands), 500 ppm fludioxonil or both. Each antifungal composition also comprised 3.2% (w/w) beeswax, 0.8% (w/w) glycerol, 0.7% (w/w) polyoxyethylene sorbitan monostearate (Tween 60), 0.1% (w/w) polyoxyethylene sorbitan monooleate (Tween 80), 0.05% (w/w) methylhydroxyethyl-cellulose (MH EC), 0.03% (w/w) anti-foaming agent, 0.02% (w/w) xanthan gum, 0.02% (w/w) citric acid, 0.01% (w/w) lactic acid and 0.01% potassium sorbate. A composition without natamycin or fludioxonil was used as control. Each composition had a pH of 4. The treated strawberries were incubated in a closed box in the dark at 20° C. for 19 days.

During incubation, mould growth on the strawberries was assessed in a twofold manner: (i) the number of moulded strawberries per total of 12 strawberries was counted; and (ii) the antifungal activity (in %) of the individual and combined active ingredients was determined by calculating the reduction in mould growth observed on the strawberries treated with the antifungal composition in comparison to the mould growth on the strawberries treated with the control composition. The expected antifungal activity (E in %) of the combined antifungal composition comprising both active ingredients was calculated according to the Colby equation (Colby, 1967):

$$E = X + Y - [(X \cdot Y)/100]$$

wherein X and Y are the observed antifungal activities (in %) of the individual active ingredients X and Y, respectively. If the observed antifungal activity (O in %) of the combination exceeds the expected antifungal activity (E in %) of the combination and the synergy factor O/E is thus >1.0, the combined application of the active ingredients leads to a synergistic antifungal effect.

The results in Table 1 (number of moulded strawberries per total of 12 strawberries) and Table 2 (antifungal activity) unequivocally demonstrate that the combined antifungal composition comprising 500 ppm natamycin and 500 ppm fludioxonil protected strawberries more effectively against mould growth than the compositions comprising natamycin or fludioxonil alone.

After 7, 8, 9, 10 and 11 days of incubation, all 12 strawberries treated with either the control composition or natamycin alone were moulded, as were respectively 3, 5, 8, 9 and 9 of the 12 strawberries treated with fludioxonil alone. However, none of the 12 strawberries treated with the active ingredient combination of natamycin and fludioxonil moulded in this 11-day incubation period (see Table 1).

On days 12 and 13, all 12 strawberries treated with either the control composition or natamycin alone were moulded, as were 9 and 11 of 12 strawberries treated with fludioxonil alone, respectively. Of the 12 strawberries treated with both natamycin and fludioxonil, however, only 1 showed mould growth on day 12 and 2 on day 13 (see Table 1).

After 14 through 17 days of incubation, all 12 strawberries treated with either the control composition, natamycin alone or fludioxonil alone were moulded. However, as many as 8, 6, 3, and 3 of the 12 strawberries treated with both natamycin and fludioxonil were still free of mould growth on day 14, 15, 16 and 17, respectively (see Table 1).

Moreover, the observed antifungal activity exceeded the expected antifungal activity with approximately 9 to >60% between 7 and 19 days of incubation. Consequently, the synergy factor was always >1.0 and increased from 1.1 on day 7 to even 12 on days 18 and 19 (see Table 2).

Thus, the combined application of 500 ppm natamycin and 500 ppm fludioxonil leads to a surprisingly strong synergistic reduction in mould growth on strawberries.

Example 6

Treatment of Strawberries

The experiment was conducted as described in Example 5, except for the fact that each wounded and inoculated strawberry was dipped individually for 1 minute in a freshly prepared aqueous antifungal composition comprising either 250 ppm natamycin (DSM Food Specialties, Delft, The Netherlands), 250 ppm fludioxonil or both. During incubation, the treated strawberries were assessed on mould growth according to the two methods described in Example 5.

The results in Table 3 (number of moulded strawberries per total of 12 strawberries) and Table 4 (antifungal activity) clearly demonstrate that the antifungal composition comprising 250 ppm natamycin and 250 ppm fludioxonil had a much stronger antifungal effect on strawberries than natamycin or fludioxonil alone.

After 6 through 9 days of incubation, all 12 strawberries treated with either the control composition were moulded, as were 11 of the 12 strawberries treated with natamycin alone. In addition, of the 12 strawberries treated with fludioxonil alone, 5 showed mould growth on days 6 through 8 and 8 on day 9. However, none of the 12 strawberries treated with the active ingredient combination of natamycin and fludioxonil moulded in this 9-day incubation period (see Table 3).

On days 10 and 11, all 12 strawberries treated with either the control composition or natamycin alone were moulded, as were 9 and 10 of 12 strawberries treated with fludioxonil alone, respectively. Of the 12 strawberries treated with both natamycin and fludioxonil, however, none displayed mould growth on day 10 and only one on day 11 (see Table 3).

After 12 through 15 days of incubation, all 12 strawberries treated with either the control composition, natamycin alone or fludioxonil alone were moulded. Among the 12 strawberries treated with both natamycin and fludioxonil, however, as many as 8, 5, 4, and 2 were still mould free on day 12, 13, 14 and 15, respectively (see Table 3).

Moreover, the observed antifungal activity was approximately 8 to 60% higher than the expected antifungal activity between 6 and 19 days of incubation. The synergy factor therefore always exceeded 1.0 and increased from 1.1 on day 6 to even >20 on days 18 and 19 (see Table 4).

Hence, the combined application of 250 ppm natamycin and 250 ppm fludioxonil has an extremely strong synergistic antifungal effect on strawberries.

Example 7

Treatment of Oranges

Eight fresh, organic oranges were used per treatment. Each orange was soaked in a 180 ppm hypochlorite solution for 10 minutes, then rinsed thoroughly with fresh tap water and dried. The peel of each disinfected orange was wounded once using a cork borer according to the method described by de Lapeyre de Bellaire and Dubois (1987). Subsequently, each wound was inoculated with 10 µl of a *Penicillium italicum* suspension containing $5\times10^5$ of spores/ml. After incubation for 3 hours at 20° C., each wound and the orange peel area of 1 cm around the wound was treated with in total 150 µl of a freshly prepared aqueous antifungal composition comprising either 500 ppm natamycin (DSM Food Specialties, Delft, The Netherlands), 300 ppm fludioxonil or both. Each antifungal composition also comprised 3.2% (w/w) beeswax, 0.8% (w/w) glycerol, 0.7% (w/w) polyoxyethylene sorbitan monostearate (Tween 60), 0.1% (w/w) polyoxyethylene sorbitan monooleate (Tween 80), 0.05% (w/w) methylhydroxyethyl-cellulose (MHEC), 0.03% (w/w) antifoaming agent, 0.02% (w/w) xanthan gum, 0.02% (w/w) citric acid, 0.01% (w/w) lactic acid and 0.01% potassium sorbate. A composition without natamycin or fludioxonil was used as control. Each composition had a pH of 4.

The treated oranges were incubated in a closed box in the dark at 20° C. and assessed on mould growth during a 27-day incubation period. The antifungal activity (in %) of the individual and combined active ingredients was determined according to the two methods described in Example 5.

The results in Table 5 (number of moulded oranges per total of 8 oranges) and Table 6 (antifungal activity) clearly reveal that the active ingredient combination of 500 ppm natamycin and 300 ppm fludioxonil was more successful in limiting mould growth on oranges than natamycin or fludioxonil alone.

After 18 through 27 days of incubation, all 8 oranges treated with the control composition were moulded, as were 6 of the 8 oranges treated with natamycin alone and 7 of the 8 oranges treated with fludioxonil alone. However, only 4 of the 8 oranges treated with the active ingredient combination of natamycin and fludioxonil were moulded between day 18 and 27 (see Table 5).

Moreover, the observed antifungal activity of the composition comprising natamycin and fludioxonil was 7 to approximately 20% higher than the expected antifungal activity between day 18 and 27. Hence, the corresponding synergy factors all exceeded >1.0 and even increased from 1.2 on day 18 to 1.7 on days 21 through 27 (see Table 6).

In conclusion, the results of this example demonstrate the strong synergistic antifungal effect of 500 ppm natamycin and 300 ppm fludioxonil when applied in combination on oranges.

Example 8

Treatment of Oranges

The experiment was conducted as described in Example 7, except for the fact that each wounded and inoculated orange was treated with 150 µl of a freshly prepared aqueous antifungal composition comprising either 250 ppm natamycin (DSM Food Specialties, Delft, The Netherlands), 100 ppm fludioxonil or both. During incubation, the treated oranges were assessed on mould growth according to the two methods described in Example 5.

The results in Table 7 (number of moulded oranges per total of 8 oranges) and Table 8 (antifungal activity) demonstrate that the active ingredient combination of 250 ppm natamycin and 100 ppm fludioxonil has a higher antifungal activity on oranges than natamycin or fludioxonil individually.

After 14 through 27 days of incubation, all 8 oranges treated with either the control composition or fludioxonil showed mould growth, as did 6 or 7 of the 8 oranges treated with natamycin alone. However, only 4 or 5 of the 8 oranges treated with the active ingredient combination of natamycin and fludioxonil were moulded between day 14 and 27 (see Table 7).

Moreover, the observed antifungal activity of the active ingredient combination of natamycin and fludioxonil was 8 to around 30% higher than the expected antifungal activity after 19 through 27 days of incubation. Consequently, the synergy factors ranged from 1.2 on day 19 to 2.8 on days 26 and 27 (see Table 8)

Thus, the combined application of 250 ppm natamycin and 100 ppm fludioxonil causes a strong synergistic reduction in mould growth on oranges.

Example 9

Treatment of Oranges

The experiment was conducted as described in Example 7, except for the fact that each wounded and inoculated orange was treated with 150 µl of a freshly prepared aqueous antifungal composition comprising either 500 ppm natamycin (DSM Food Specialties, Delft, The Netherlands), 400 ppm fenpiclonil or both. During a 23-day incubation period, the treated oranges were assessed on mould growth according to the two methods described in Example 5.

The results in Table 9 (number of moulded oranges per total of 8 oranges) and Table 10 (antifungal activity) clearly reveal that the active ingredient combination of 500 ppm natamycin and 400 ppm fenpiclonil was more successful in limiting mould growth on oranges than natamycin or fenpiclonil alone.

After 14 and 15 days of incubation, all 8 oranges treated with the control composition, 5 of the 8 oranges treated with natamycin alone and 6 of the 8 oranges treated with fenpiclonil alone showed mould growth. However, only 2 of the 8 oranges treated with the active ingredient combination of natamycin and fenpiclonil were moulded on days 14 and 15 (see Table 9).

On days 16, 18 and 19 through 23, all 8 oranges treated with either the control composition or fenpiclonil alone were moulded, in addition to 5 or 6 of the 8 oranges treated with natamycin alone were moulded. Among the 8 oranges treated with the active ingredient combination of natamycin and fenpiclonil, however, only 2, 3 and 4 displayed mould growth on days 16, 18 and 19 through 23, respectively (see Table 9).

Moreover, the observed antifungal activity of the composition comprising natamycin and fenpiclonil was 8 to 40% higher than the expected antifungal activity between 12 and 23 days of incubation. Hence, the corresponding synergy factors were all >1.0 and increased from 1.1 on day 12 to 3.6 on days 22 and 23 (see Table 10).

In conclusion, the results of this example clearly demonstrate the synergistic antifungal effect of 500 ppm natamycin and 400 ppm fenpiclonil when applied in combination on oranges.

Example 10

Treatment of Sweet Peppers

Ten fresh, organic sweet peppers were used per treatment. The peel of each sweet pepper was wounded once using a cork borer according to the method described by de Lapeyre de Bellaire and Dubois (1987). Subsequently, each wound was inoculated with 10 μl of a Botrytis cinerea suspension containing $1 \times 10^5$ of spores/ml. After incubation for 3 hours at 20° C., each wound and the skin area of 0.5 cm around the wound was treated with in total 75 μl of a freshly prepared aqueous antifungal composition comprising either 400 ppm natamycin (DSM Food Specialties, Delft, The Netherlands), 600 ppm fenpiclonil or both. Each antifungal composition also comprised 3.2% (w/w) beeswax, 0.8% (w/w) glycerol, 0.7% (w/w) polyoxyethylene sorbitan monostearate (Tween 60), 0.2% (w/w) polyoxyethylene sorbitan monooleate (Tween 80), 0.05% (w/w) methylhydroxyethyl-cellulose (MHEC), 0.03% (w/w) anti-foaming agent, 0.02% (w/w) xanthan gum, 0.02% (w/w) citric acid, 0.01% (w/w) lactic acid and 0.01% potassium sorbate. A composition without natamycin or fenpiclonil was used as control. Each composition had a pH of 4.

The treated sweet peppers were incubated in a closed box in the dark at 20° C. and assessed on mould growth during incubation. The antifungal activity (in %) of the individual and combined active ingredients was determined by calculating the reduction in mould growth observed on the sweet peppers treated with the antifungal composition in comparison to the mould growth on the sweet peppers treated with the control composition according to the Colby method (Colby, 1967) as described in Example 5.

The results in Table 11 show that the combined antifungal composition comprising 400 ppm natamycin and 600 ppm fenpiclonil protected sweet peppers more effectively against mould growth than the compositions comprising either natamycin or fenpiclonil.

After 47 through 50 days of incubation, the observed antifungal activity of the active ingredient combination of natamycin and fenpiclonil exceeded the expected antifungal activity with approximately 30 to 45%, which resulted in synergy factors between 4.0 and 14.0 (see Table 11).

Thus, this example proves the synergistic antifungal effect of the combined application of 400 ppm natamycin and 600 ppm fenpiclonil on sweet peppers.

Example 11

Treatment of Pineapples

In this experiment pineapples were selected from a packing plant located in Costa Rica. These pineapples were selected based on uniformity in color and size. Furthermore, they were free from visual mold growth or any other visual damage caused by plagues or diseases.

The surface of the pineapples was first disinfected by immersion of the fruits for one minute in a solution comprising 150 ppm sodium hypochlorite. Next, the fruits were dried and thereafter the antimicrobial compositions were applied on the fruits using a modified watering can. This shower, to simulate the wax cascade used in pineapple packing plants, covered the rind of the fruits with a thin film of wax. The crown of the pineapple was not treated. The following antimicrobial compositions were applied on the fruits:

Composition A: aqueous composition comprising 20% v/v wax (STA FRESH 2952);

Composition B: aqueous composition comprising 200 ppm of natamycin (DSM Food Specialties, Delft, The Netherlands) and 20% v/v wax (STA FRESH 2952);

Composition C: aqueous composition comprising 250 ppm of fludioxonil and 20% v/v wax (STA FRESH 2952);

Composition D: aqueous composition comprising 200 ppm of natamycin, 250 ppm of fludioxonil and 20% v/v wax (STA FRESH 2952).

The experiment was done in forty fold (5 boxes per composition, each box comprising 8 pineapples). All compositions had a pH of 7.2. In addition, the respective compositions were sprayed onto the peduncle (the wound) of each of the treated fruits at a rate of 1 ml per fruit. After application of the compositions, the pineapples were dried.

To simulate transportation of the pineapples in a shipping container, the pineapples were stored in a cold chamber at a temperature of 7.5° C. for 21 days. After 21 days, the temperature was raised to 18 to 20° C. to simulate shelf-life in a supermarket. The pineapples were stored for another 7 days at 18 to 20° C. Thus, the total storage time was 28 days.

After 28 days, the mould incidence on the pineapple rinds was assessed using the following method. The number of pineapples with visual mould incidence on the rind per total of 40 pineapples was counted for all compositions. Subsequently, the antifungal activity (in %) of the individual and combined active ingredients (compositions B, C and D) was determined by calculating the reduction in mould incidence observed on the pineapple rind compared to composition A. The observed antifungal activity of composition D was compared to the expected antifungal activity of composition D according to the Colby method (Colby, 1967) as described in Example 5.

The results (see Table 12) demonstrate that the antifungal composition comprising 200 ppm natamycin and 250 ppm fludioxonil have a stronger antifungal activity on pineapples than natamycin or fludioxonil alone.

Hence, the combined application of natamycin and fludioxonil synergistically reduces mould growth on pineapples.

TABLE 1

Number of moulded strawberries incubated at 20° C. after treatment with compositions comprising either 500 ppm natamycin, 500 ppm fludioxonil or both.

| Antifungal Composition | Number of moulded strawberries/ total number of 12 strawberries during incubation time (in days) | | | | | | | | |
|---|---|---|---|---|---|---|---|---|---|
| | Day 7 | Day 8 | Day 9 | Day 10-11 | Day 12 | Day 13 | Day 14 | Day 15 | Day 16-17 |
| Control | 12/12 | 12/12 | 12/12 | 12/12 | 12/12 | 12/12 | 12/12 | 12/12 | 12/12 |
| Natamycin 500 ppm | 12/12 | 12/12 | 12/12 | 12/12 | 12/12 | 12/12 | 12/12 | 12/12 | 12/12 |
| Fludioxonil 500 ppm | 3/12 | 5/12 | 8/12 | 9/12 | 9/12 | 11/12 | 12/12 | 12/12 | 12/12 |

TABLE 1-continued

Number of moulded strawberries incubated at 20° C. after treatment with compositions comprising either 500 ppm natamycin, 500 ppm fludioxonil or both.

| Antifungal Composition | Day 7 | Day 8 | Day 9 | Day 10-11 | Day 12 | Day 13 | Day 14 | Day 15 | Day 16-17 |
|---|---|---|---|---|---|---|---|---|---|
| Natamycin 500 ppm + fludioxonil 500 ppm | 0/12 | 0/12 | 0/12 | 0/12 | 1/12 | 2/12 | 4/12 | 6/12 | 9/12 |

TABLE 2

Antifungal activity (%) of compositions comprising either 500 ppm natamycin, 500 ppm fludioxonil or both on strawberries after incubation at 20° C.

| Antifungal composition | Incubation time (days) | Observed antifungal activity O (%) | Expected antifungal activity E (%) | Synergy factor O/E |
|---|---|---|---|---|
| Control | 7 | 0 | — | — |
| Natamycin 500 ppm | | 11 | — | — |
| Fludioxonil 500 ppm | | 90 | — | — |
| Natamycin 500 ppm + fludioxonil 500 ppm | | 100 | 91 | 1.1 |
| Control | 8 | 0 | — | — |
| Natamycin 500 ppm | | 14 | — | — |
| Fludioxonil 500 ppm | | 80 | — | — |
| Natamycin 500 ppm + fludioxonil 500 ppm | | 100 | 83 | 1.2 |
| Control | 9 | 0 | — | — |
| Natamycin 500 ppm | | 4.8 | — | — |
| Fludioxonil 500 ppm | | 67 | — | — |
| Natamycin 500 ppm + fludioxonil 500 ppm | | 100 | 68 | 1.5 |
| Control | 10 | 0 | — | — |
| Natamycin 500 ppm | | 2.4 | — | — |
| Fludioxonil 500 ppm | | 56 | — | — |
| Natamycin 500 ppm + fludioxonil 500 ppm | | 100 | 57 | 1.8 |
| Control | 11 | 0 | — | — |
| Natamycin 500 ppm | | 2.4 | — | — |
| Fludioxonil 500 ppm | | 52 | — | — |
| Natamycin 500 ppm + fludioxonil 500 ppm | | 100 | 54 | 1.9 |
| Control | 12 | 0 | — | — |
| Natamycin 500 ppm | | 0 | — | — |
| Fludioxonil 500 ppm | | 44 | — | — |
| Natamycin 500 ppm + fludioxonil 500 ppm | | 98 | 44 | 2.2 |
| Control | 13 | 0 | — | — |
| Natamycin 500 ppm | | 0 | — | — |
| Fludioxonil 500 ppm | | 33 | — | — |
| Natamycin 500 ppm + fludioxonil 500 ppm | | 94 | 33 | 2.8 |
| Control | 14 | 0 | — | — |
| Natamycin 500 ppm | | 0 | — | — |
| Fludioxonil 500 ppm | | 24 | — | — |
| Natamycin 500 ppm + fludioxonil 500 ppm | | 90 | 24 | 3.8 |
| Control | 15 | 0 | — | — |
| Natamycin 500 ppm | | 0 | — | — |
| Fludioxonil 500 ppm | | 17 | — | — |
| Natamycin 500 ppm + fludioxonil 500 ppm | | 81 | 17 | 4.8 |
| Control | 16 | 0 | — | — |
| Natamycin 500 ppm | | 0 | — | — |
| Fludioxonil 500 ppm | | 13 | — | — |
| Natamycin 500 ppm + fludioxonil 500 ppm | | 73 | 13 | 5.6 |
| Control | 18 | 0 | — | — |
| Natamycin 500 ppm | | 0 | — | — |
| Fludioxonil 500 ppm | | 4.8 | — | — |

TABLE 2-continued

Antifungal activity (%) of compositions comprising either 500 ppm natamycin, 500 ppm fludioxonil or both on strawberries after incubation at 20° C.

| Antifungal composition | Incubation time (days) | Observed antifungal activity O (%) | Expected antifungal activity E (%) | Synergy factor O/E |
|---|---|---|---|---|
| Natamycin 500 ppm + fludioxonil 500 ppm | | 56 | 4.8 | 12 |
| Control | 19 | 0 | — | — |
| Natamycin 500 ppm | | 0 | — | — |
| Fludioxonil 500 ppm | | 3.6 | — | — |
| Natamycin 500 ppm + fludioxonil 500 ppm | | 44 | 3.6 | 12 |

TABLE 3

Number of moulded strawberries incubated at 20° C. after treatment with compositions comprising either 250 ppm natamycin, 250 ppm fludioxonil or both.

| Antifungal composition | Day 6-8 | Day 9 | Day 10 | Day 11 | Day 12 | Day 13 | Day 14 | Day 15 |
|---|---|---|---|---|---|---|---|---|
| Control | 12/12 | 12/12 | 12/12 | 12/12 | 12/12 | 12/12 | 12/12 | 12/12 |
| Natamycin 250 ppm | 11/12 | 11/12 | 12/12 | 12/12 | 12/12 | 12/12 | 12/12 | 12/12 |
| Fludioxonil 250 ppm | 5/12 | 8/12 | 9/12 | 10/12 | 12/12 | 12/12 | 12/12 | 12/12 |
| Natamycin 250 ppm + fludioxonil 250 ppm | 0/12 | 0/12 | 0/12 | 1/12 | 4/12 | 7/12 | 8/12 | 10/12 |

TABLE 4

Antifungal activity (%) of compositions comprising either 250 ppm natamycin, 250 ppm fludioxonil or both on strawberries after incubation at 20° C.

| Antifungal composition | Incubation time (days) | Observed antifungal activity O (%) | Expected antifungal activity E (%) | Synergy factor O/E |
|---|---|---|---|---|
| Control | 6 | 0 | — | — |
| Natamycin 250 ppm | | 23 | — | — |
| Fludioxonil 250 ppm | | 89 | — | — |
| Natamycin 250 ppm + fludioxonil 250 ppm | | 100 | 92 | 1.1 |
| Control | 7 | 0 | — | — |
| Natamycin 250 ppm | | 23 | — | — |
| Fludioxonil 250 ppm | | 81 | — | — |
| Natamycin 250 ppm + fludioxonil 250 ppm | | 100 | 86 | 1.2 |
| Control | 8 | 0 | — | — |
| Natamycin 250 ppm | | 18 | — | — |
| Fludioxonil 250 ppm | | 81 | — | — |
| Natamycin 250 ppm + fludioxonil 250 ppm | | 100 | 85 | 1.2 |
| Control | 9 | 0 | — | — |
| Natamycin 250 ppm | | 13 | — | — |
| Fludioxonil 250 ppm | | 69 | — | — |
| Natamycin 250 ppm + fludioxonil 250 ppm | | 100 | 73 | 1.4 |
| Control | 10 | 0 | — | — |
| Natamycin 250 ppm | | 4.8 | — | — |
| Fludioxonil 250 ppm | | 55 | — | — |
| Natamycin 250 ppm + fludioxonil 250 ppm | | 100 | 57 | 1.8 |
| Control | 11 | 0 | — | — |
| Natamycin 250 ppm | | 4.8 | — | — |
| Fludioxonil 250 ppm | | 44 | — | — |
| Natamycin 250 ppm + fludioxonil 250 ppm | | 99 | 47 | 2.1 |
| Control | 12 | 0 | — | — |
| Natamycin 250 ppm | | 1.2 | — | — |
| Fludioxonil 250 ppm | | 32 | — | — |
| Natamycin 250 ppm + fludioxonil 250 ppm | | 90 | 33 | 2.7 |
| Control | 13 | 0 | — | — |
| Natamycin 250 ppm | | 1.2 | — | — |
| Fludioxonil 250 ppm | | 26 | — | — |
| Natamycin 250 ppm + fludioxonil 250 ppm | | 83 | 27 | 3.1 |
| Control | 14 | 0 | — | — |
| Natamycin 250 ppm | | 1.2 | — | — |
| Fludioxonil 250 ppm | | 19 | — | — |
| Natamycin 250 ppm + fludioxonil 250 ppm | | 76 | 20 | 3.8 |
| Control | 15 | 0 | — | — |
| Natamycin 250 ppm | | 0 | — | — |
| Fludioxonil 250 ppm | | 11 | — | — |
| Natamycin 250 ppm + fludioxonil 250 ppm | | 70 | 11 | 6.4 |
| Control | 16 | 0 | — | — |
| Natamycin 250 ppm | | 0 | — | — |
| Fludioxonil 250 ppm | | 6.0 | — | — |
| Natamycin 250 ppm + fludioxonil 250 ppm | | 57 | 6.0 | 9.5 |
| Control | 18 | 0 | — | — |
| Natamycin 250 ppm | | 0 | — | — |
| Fludioxonil 250 ppm | | 1.2 | — | — |
| Natamycin 250 ppm + fludioxonil 250 ppm | | 35 | 1.2 | 29 |
| Control | 19 | 0 | — | — |
| Natamycin 250 ppm | | 0 | — | — |
| Fludioxonil 250 ppm | | 0 | — | — |
| Natamycin 250 ppm + fludioxonil 250 ppm | | 20 | 0 | >20 |

TABLE 5

Number of moulded oranges incubated at 20° C. after treatment with compositions comprising either 500 ppm natamycin, 300 ppm fludioxonil or both.

| Antifungal composition | Number of moulded oranges/ total number of 8 oranges during incubation time (in days) Day 18-27 |
|---|---|
| Control | 8/8 |
| Natamycin 500 ppm | 6/8 |
| Fludioxonil 300 ppm | 7/8 |
| Natamycin 500 ppm + fludioxonil 300 ppm | 4/8 |

TABLE 6

Antifungal activity (%) of compositions comprising either 500 ppm natamycin, 300 ppm fludioxonil or both on oranges after incubation at 20° C.

| Antifungal composition | Incubation time (days) | Observed antifungal activity O (%) | Expected antifungal activity E (%) | Synergy factor O/E |
|---|---|---|---|---|
| Control | 18 | 0 | — | — |
| Natamycin 500 ppm | | 32 | — | — |
| Fludioxonil 300 ppm | | 17 | — | — |
| Natamycin 500 ppm + fludioxonil 300 ppm | | 50 | 43 | 1.2 |
| Control | 19 | 0 | — | — |
| Natamycin 500 ppm | | 29 | — | — |
| Fludioxonil 300 ppm | | 17 | — | — |
| Natamycin 500 ppm + fludioxonil 300 ppm | | 50 | 40 | 1.3 |
| Control | 20 | 0 | — | — |
| Natamycin 500 ppm | | 20 | — | — |
| Fludioxonil 300 ppm | | 17 | — | — |
| Natamycin 500 ppm + fludioxonil 300 ppm | | 50 | 33 | 1.5 |
| Control | 21 | 0 | — | — |
| Natamycin 500 ppm | | 16 | — | — |
| Fludioxonil 300 ppm | | 17 | — | — |
| Natamycin 500 ppm + fludioxonil 300 ppm | | 50 | 30 | 1.7 |
| Control | 22-27 | 0 | — | — |
| Natamycin 500 ppm | | 14 | — | — |
| Fludioxonil 300 ppm | | 17 | — | — |
| Natamycin 500 ppm + fludioxonil 300 ppm | | 50 | 29 | 1.7 |

TABLE 7

Number of moulded oranges incubated at 20° C. after treatment with compositions comprising either 250 ppm natamycin, 100 ppm fludioxonil or both.

| Antifungal composition | Number of moulded oranges/ total number of 8 oranges during incubation time (in days) | | |
|---|---|---|---|
| | Day 14-18 | Day 19-22 | Day 23-27 |
| Control | 8/8 | 8/8 | 8/8 |
| Natamycin 250 ppm | 6/8 | 7/8 | 7/8 |
| Fludioxonil 100 ppm | 8/8 | 8/8 | 8/8 |
| Natamycin 250 ppm + fludioxonil 100 ppm | 4/8 | 4/8 | 5/8 |

TABLE 8

Antifungal activity (%) of compositions comprising either 250 ppm natamycin, 100 ppm fludioxonil or both on oranges after incubation at 20° C.

| Antifungal composition | Incubation time (days) | Observed antifungal activity O (%) | Expected antifungal activity E (%) | Synergy factor O/E |
|---|---|---|---|---|
| Control | 19 | 0 | — | — |
| Natamycin 250 ppm | | 36 | — | — |
| Fludioxonil 100 ppm | | 9 | — | — |
| Natamycin 250 ppm + fludioxonil 100 ppm | | 50 | 42 | 1.2 |
| Control | 20 | 0 | — | — |
| Natamycin 250 ppm | | 34 | — | — |
| Fludioxonil 100 ppm | | 2 | — | — |
| Natamycin 250 ppm + fludioxonil 100 ppm | | 50 | 35 | 1.4 |
| Control | 21 | 0 | — | — |
| Natamycin 250 ppm | | 32 | — | — |
| Fludioxonil 100 ppm | | 0 | — | — |
| Natamycin 250 ppm + fludioxonil 100 ppm | | 50 | 32 | 1.6 |
| Control | 22 | 0 | — | — |
| Natamycin 250 ppm | | 29 | — | — |
| Fludioxonil 100 ppm | | 0 | — | — |
| Natamycin 250 ppm + fludioxonil 100 ppm | | 50 | 29 | 1.7 |
| Control | 23 | 0 | — | — |
| Natamycin 250 ppm | | 25 | — | — |
| Fludioxonil 100 ppm | | 0 | — | — |
| Natamycin 250 ppm + fludioxonil 100 ppm | | 48 | 25 | 1.9 |
| Control | 25 | 0 | — | — |
| Natamycin 250 ppm | | 19 | — | — |
| Fludioxonil 100 ppm | | 0 | — | — |
| Natamycin 250 ppm + fludioxonil 100 ppm | | 48 | 19 | 2.5 |
| Control | 26-27 | 0 | — | — |
| Natamycin 250 ppm | | 17 | — | — |
| Fludioxonil 100 ppm | | 0 | — | — |
| Natamycin 250 ppm + fludioxonil 100 ppm | | 48 | 17 | 2.8 |

TABLE 9

Number of moulded oranges incubated at 20° C. after treatment with compositions comprising either 500 ppm natamycin, 400 ppm fenpiclonil or both.

| Antifungal composition | Number of moulded oranges/ total number of 8 oranges during incubation time (in days) | | | |
|---|---|---|---|---|
| | Day 14-15 | Day 16 | Day 18 | Day 19-23 |
| Control | 8/8 | 8/8 | 8/8 | 8/8 |
| Natamycin 500 ppm | 5/8 | 5/8 | 6/8 | 6/8 |
| Fenpiclonil 400 ppm | 6/8 | 8/8 | 8/8 | 8/8 |
| Natamycin 500 ppm + fenpiclonil 400 ppm | 2/8 | 2/8 | 3/8 | 4/8 |

TABLE 10

Antifungal activity (%) of compositions comprising either 500 ppm natamycin, 400 ppm fenpiclonil or both on oranges after incubation at 20° C.

| Antifungal composition | Incubation time (days) | Observed antifungal activity O (%) | Expected antifungal activity E (%) | Synergy factor O/E |
|---|---|---|---|---|
| Control | 12 | 0 | — | — |
| Natamycin 500 ppm | | 55 | — | — |
| Fenpiclonil 400 ppm | | 78 | — | — |
| Natamycin 500 ppm + fenpiclonil 400 ppm | | 98 | 90 | 1.1 |
| Control | 13 | 0 | — | — |
| Natamycin 500 ppm | | 52 | — | — |
| Fenpiclonil 400 ppm | | 70 | — | — |
| Natamycin 500 ppm + fenpiclonil 400 ppm | | 94 | 86 | 1.1 |
| Control | 14 | 0 | — | — |
| Natamycin 500 ppm | | 48 | — | — |
| Fenpiclonil 400 ppm | | 66 | — | — |
| Natamycin 500 ppm + fenpiclonil 400 ppm | | 92 | 82 | 1.1 |
| Control | 15 | 0 | — | — |
| Natamycin 500 ppm | | 45 | — | — |
| Fenpiclonil 400 ppm | | 59 | — | — |
| Natamycin 500 ppm + fenpiclonil 400 ppm | | 90 | 78 | 1.1 |
| Control | 16 | 0 | — | — |
| Natamycin 500 ppm | | 43 | — | — |
| Fenpiclonil 400 ppm | | 47 | — | — |
| Natamycin 500 ppm + fenpiclonil 400 ppm | | 85 | 70 | 1.2 |
| Control | 18 | 0 | — | — |
| Natamycin 500 ppm | | 32 | — | — |
| Fenpiclonil 400 ppm | | 28 | — | — |
| Natamycin 500 ppm + fenpiclonil 400 ppm | | 81 | 51 | 1.6 |
| Control | 19 | 0 | — | — |
| Natamycin 500 ppm | | 29 | — | — |
| Fenpiclonil 400 ppm | | 17 | — | — |
| Natamycin 500 ppm + fenpiclonil 400 ppm | | 73 | 41 | 1.8 |
| Control | 20 | 0 | — | — |
| Natamycin 500 ppm | | 20 | — | — |
| Fenpiclonil 400 ppm | | 6 | — | — |
| Natamycin 500 ppm + fenpiclonil 400 ppm | | 65 | 25 | 2.6 |
| Control | 21 | 0 | — | — |
| Natamycin 500 ppm | | 16 | — | — |
| Fenpiclonil 400 ppm | | 3 | — | — |
| Natamycin 500 ppm + fenpiclonil 400 ppm | | 54 | 19 | 2.8 |
| Control | 22-23 | 0 | — | — |
| Natamycin 500 ppm | | 14 | — | — |
| Fenpiclonil 400 ppm | | 0 | — | — |
| Natamycin 500 ppm + fenpiclonil 400 ppm | | 50 | 14 | 3.6 |

TABLE 11

Antifungal activity (%) of compositions comprising either 400 ppm natamycin, 600 ppm fenpiclonil or both on sweet peppers after incubation at 20° C.

| Antifungal composition | Incubation time (days) | Observed antifungal activity O (%) | Expected antifungal activity E (%) | Synergy factor O/E |
|---|---|---|---|---|
| Control | 47 | 0 | — | — |
| Natamycin 400 ppm | | 15 | — | — |
| Fenpiclonil 600 ppm | | 0 | — | — |
| Natamycin 400 ppm + Fenpiclonil 600 ppm | | 60 | 15 | 4.0 |
| Control | 48 | 0 | — | — |
| Natamycin 400 ppm | | 6 | — | — |
| Fenpiclonil 600 ppm | | 0 | — | — |
| Natamycin 400 ppm + Fenpiclonil 600 ppm | | 48 | 6 | 7.6 |
| Control | 49 | 0 | — | — |
| Natamycin 400 ppm | | 4 | — | — |
| Fenpiclonil 600 ppm | | 0 | — | — |
| Natamycin 400 ppm + Fenpiclonil 600 ppm | | 41 | 4 | 11.0 |
| Control | 50 | 0 | — | — |
| Natamycin 400 ppm | | 3 | — | — |
| Fenpiclonil 600 ppm | | 0 | — | — |
| Natamycin 400 ppm + Fenpiclonil 600 ppm | | 35 | 3 | 14.0 |

TABLE 12

Antifungal activity (%) of compositions comprising either 200 ppm natamycin, 250 ppm fludioxonil or both on pineapples after 28 days of storage (21 days at 7.5° C. and subsequently 7 days at 18 to 20° C.).

| Antifungal composition | Observed Antifungal activity O (%) | Expected antifungal activity E (%) | Synergy factor O/E |
|---|---|---|---|
| Control | 0 | — | — |
| Natamycin 200 ppm | 35 | — | — |
| Fludioxonil 250 ppm | 90 | — | — |
| Natamycin 200 ppm + Fludioxonil 250 ppm | 97.5 | 93.5 | 1.04 |

REFERENCES

Colby S R (1967), Calculating synergistic and antagonistic responses of herbicide combination. Weeds 15: 20-22.

Iacomi-Vasilescu B, Avenot H, Bataille-Simoneau N, Laurent E, Guenard M and Simoneau P (2004), In vitro fungicide sensitivity of *Alternaria* species pathogenic to crucifers and identification of *Alternaria brassicicola* field isolates highly resistant to both dicarboximides and phenylpyrroles. Crop Prot. 23: 481-488.

Kanetis L, Forster H and Adaskaveg J E (2006), Fludioxonil-resistant isolates of *Penicillium digitatum* show diverse fitness and no relationship to osmotic stress regulation. (Abstr.) Phytopathology 96 (suppl.): S58.

Kinay P, Mansour M F, Gabler F M, Margosan D A and Smilanick J L (2007), Characterization of fungicide-resistant isolates of *Penicillium digitatum* collected in California. Crop Prot. 26: 647-656.

Slinker B K (1998), The Statistics of Synergism. Journal of Mol. and Cell. Cardiology 30:723-731.

The invention claimed is:
1. A composition comprising a polyene antifungal compound and at least one antifungal compound from the family of phenylpyrrole fungicides wherein the polyene antifungal compound is natamycin and the at least one antifungal compound from the family of phenylpyrrole fungicides is selected from the group consisting of fludioxonil and fenpiclonil.

2. A composition according to claim 1, wherein the composition further comprises at least one additional compound selected from the group consisting of a sticking agent, a carrier, a colouring agent, a protective colloid, an adhesive, a herbicide, a fertilizer, a thickening agent, a sequestering agent, a thixotropic agent, a surfactant, a further antimicrobial compound, a detergent, a preservative, a spreading agent, a filler, a spray oil, a flow additive, a mineral substance, a solvent, a dispersant, an emulsifier, a wetting agent, a stabiliser, an antifoaming agent, a buffering agent, an UV-absorber and an antioxidant.

3. A composition according to claim 1, wherein the amount of the polyene antifungal compound is in a range from 0.005 g/l to about 100 g/l and the amount of the at least one antifungal compound from the family of phenylpyrrole fungicides is in a range from about 0.0001 g/l to about 2000 g/l.

4. A composition according to claim 3, wherein the amount of the polyene antifungal compound is in a range from about 0.01 g/l to about 3 g/l.

5. A composition according to claim 3, wherein the amount of the at least one antifungal compound from the family of phenylpyrrole fungicides is in a range from about 0.001 g/l to about 1000 g/l.

6. A composition according to claim 1, wherein the at least one antifungal compound from the family of phenylpyrrole fungicides is fludioxonil.

7. A composition according to claim 1, wherein the at least one antifungal compound from the family of phenylpyrrole fungicides is fenpiclonil.

8. A composition according to claim 1, wherein the antifungal activity of the composition is synergistic.

9. A method for protecting a product against fungi comprising treating the product with the composition of claim 1.

10. A method according to claim 9, wherein the product is selected from the group consisting of a food product, a feed product, a pharmaceutical product, a cosmetic product and an agricultural product.

11. A method according to claim 10, wherein the product is an agricultural product.

12. A method according to claim 11, wherein the product is treated post-harvest.

13. A kit comprising a polyene antifungal compound and at least one antifungal compound from the family of phenylpyrrole fungicides, wherein the polyene antifungal compound is natamycin and the at least one antifungal compound from the family of phenylpyrrole fungicides is selected from the group consisting of fludioxonil and fenpiclonil.

14. A product comprising a polyene antifungal compound and at least one antifungal compound from the family of phenylpyrrole fungicides, wherein the polyene antifungal compound is natamycin and the at least one antifungal compound from the family of phenylpyrrole fungicides is selected from the group consisting of fludioxonil and fenpiclonil.

15. A product according to claim 14, wherein the product is selected from the group consisting of a food product, a feed product, a pharmaceutical product, a cosmetic product and an agricultural product.

16. A product according to claim 15, wherein the product is an agricultural product.

17. A product according to claim 16, wherein the agricultural product is a fruit.

18. A product according to claim 16, wherein the agricultural product is a vegetable.

\* \* \* \* \*